United States Patent
Nelson et al.

(10) Patent No.: US 10,837,065 B2
(45) Date of Patent: Nov. 17, 2020

(54) METHODS FOR TEMPERATURE-MEDIATED NESTED POLYMERASE CHAIN REACTION

(71) Applicant: Tetracore, Inc., Rockville, MD (US)

(72) Inventors: William M. Nelson, Rockville, MD (US); Kyle Armantrout, Los Angeles, CA (US); Tracy Calvin Fecteau, Ellicott City, MD (US)

(73) Assignee: TETRACORE, INC., Rockville, MD (US)

( * ) Notice: Subject to any disclaimer, the term of this patent is extended or adjusted under 35 U.S.C. 154(b) by 0 days.

(21) Appl. No.: 15/235,596

(22) Filed: Aug. 12, 2016

(65) Prior Publication Data

US 2017/0044585 A1 Feb. 16, 2017

Related U.S. Application Data

(60) Provisional application No. 62/205,248, filed on Aug. 14, 2015.

(51) Int. Cl.
*C12Q 1/689* (2018.01)
*C12Q 1/6844* (2018.01)
*C12Q 1/70* (2006.01)

(52) U.S. Cl.
CPC .......... *C12Q 1/689* (2013.01); *C12Q 1/6844* (2013.01); *C12Q 1/701* (2013.01)

(58) Field of Classification Search
None
See application file for complete search history.

(56) References Cited

U.S. PATENT DOCUMENTS

| | | | |
|---|---|---|---|
| 2006/0068433 A1* | 3/2006 | Godfrey | C12Q 1/6851 435/6.18 |
| 2010/0304444 A1* | 12/2010 | Morley | C12Q 1/686 435/91.2 |

OTHER PUBLICATIONS

Weller et al., "Detection of Ralstonia Solanacearum Strains with a Quantitative, Multiplex, Real-Time, Fluorogenic PCR (TaqMan) Assay," Applied and Environmental Microbiology, July, vol. 66, No. 7, pp. 2853-2858 (Year: 2000).*

(Continued)

*Primary Examiner* — Young J Kim
(74) *Attorney, Agent, or Firm* — Finnegan, Henderson, Farabow, Garrett & Dunner LLP

(57) ABSTRACT

Embodiments of present disclosure are directed to methods for amplifying nucleic acid, comprising two steps: a first step of preparing a reaction mixture comprising the target nucleic acid and a second step of processing the reaction mixture in a thermocycler. During a first phase of the processing step, the thermocycler may be configured to heat the reaction mixture to a first temperature and cool the reaction mixture to a second temperature repeatedly for a first plurality of cycles. During the first phase, fluorescence probes do not anneal to template strands and do not emit fluorescence signals. During a second phase of the processing step, the thermocycler may heat the reaction mixture to a third temperature and cool the reaction mixture to a fourth temperature repeatedly for a second plurality of cycles. During the second phase, fluorescence probes anneal to the template strands and are degraded by DNA polymerase to emit fluorescence signals for detection and/or quantification of the target nucleic acid. Methods for amplifying nucleic acid in accordance with the disclosure may be employed for nucleic acid amplification and detection in clinical and research settings.

14 Claims, 4 Drawing Sheets

(56) References Cited

OTHER PUBLICATIONS

Melting Temperature Calculation, [retrieved on-line: http://biotools.nubic.northwestern.edu/OligoCalc.html, retrival date: Mar. 13, 2018], pp. 1-5.*

* cited by examiner

METHODS FOR TEMPERATURE-MEDIATED NESTED POLYMERASE CHAIN REACTION

PRIORITY CLAIM

This application claims priority from U.S. Provisional Patent Application No. 62/205,248 filed on Aug. 14, 2015, which is hereby incorporated by reference in its entirety in the present application.

TECHNICAL FIELD

The present disclosure generally relates to methods and systems for nucleic acid amplification reactions, and more specifically, to methods and systems for polymerase chain reaction.

BACKGROUND

Polymerase chain reaction (PCR) is a technique routinely used in molecular biology for amplifying nucleic acids, such as DNA. PCR is both a thermodynamic and an enzymatic process. PCR uses DNA polymerase, an enzyme that catalyzes DNA replication, to synthesize a new strand of DNA complementary to a template strand. DNA polymerase requires a primer, a short strand of nucleic acid sequence that can anneal or bind to the template strand and to which it can add new nucleotides. By selecting a specific primer, it is possible to specify a target sequence of the template DNA to amplify. During PCR, the target DNA being amplified is heated to separate the double-stranded helix. Then, upon cooling, the primers anneal or bind to each DNA strand, creating a starting point for the addition of nucleotides. The process is repeated until many copies of the target DNA are created. The amplified copies of the target DNA can be detected and quantified using fluorescence probes and detectors. Many applications of PCR have been developed for both clinical diagnosis and basic research, such as pathogen detection, microbial assessment of food and water, measurement of gene expression, genotyping, and infectious disease and cancer diagnosis.

A typical PCR process includes a number of repeated thermal cycles of heating and cooling and can take from one hour to a few hours. Some major applications of PCR are challenging the current PCR technologies and demand faster turnaround from sample to results and increased throughput. For example, fast PCR processes can be beneficial to applications such as infectious disease detection in a point-of-care setting, where fast and early diagnosis can be crucial for the control and treatment of the disease. Methods to reduce the time of the PCR process include using a smaller volume of the PCR reaction mixture and thus a smaller volume of the sample to be tested. However, using a smaller sample volume may further reduce the probability to amplify or detect the target sequences that exist in very low concentrations. Other methods may include using special high-speed DNA polymerase, which, however, the activity of these enzymes may be affected by enzyme and/or template concentrations. Therefore, methods that reduce the time and thus improve the throughput of the PCR process are desirable.

SUMMARY

The present disclosure is directed to methods for amplifying nucleic acid. In one embodiment, the method includes preparing a reaction mixture including at least one target nucleic acid and processing the reaction mixture in a thermocycler. In some embodiments, the processing includes heating the reaction mixture to a first temperature and cooling the reaction mixture to a second temperature repeatedly for a first plurality of cycles. In some embodiments, the processing further includes heating the reaction mixture to a third temperature and cooling the reaction mixture to a fourth temperature repeatedly for a second plurality of cycles.

In some embodiments, the reaction mixture includes at least one probe configured to emit a fluorescence signal upon excitation. In some embodiments, the probe is configured to have a melting temperature lower than the second temperature. In some embodiments, the probe is configured to have a melting temperature higher than the fourth temperature. In some embodiments, the probe is configured to anneal to the target nucleic acid at the fourth temperature. In some embodiments, the processing includes detecting the fluorescence signal during the second plurality of cycles.

In some embodiments, the reaction mixture includes a first set of primers configured to have melting temperatures around the second temperature and anneal to the target nucleic acid at the second temperature. In some embodiments, the reaction mixture includes a second set of primers configured to have melting temperatures around the fourth temperature and anneal to the target nucleic acid at the fourth temperature. In some embodiments, the melting temperatures of the first set of primers may be higher than those of the second set of primers.

In some embodiments, both of the first temperature and the third temperature may range from 85° C. to 100° C. In some embodiments, the second temperature may be higher than the fourth temperature. In some embodiments, the second temperature may range from 70° C. to 85° C. In some embodiments, the fourth temperature may range from 55° C. to 70° C.

Other embodiments of this disclosure are contained in the accompanying drawings, description, and claims. Thus, this summary is exemplary only, and is not to be considered restrictive.

BRIEF DESCRIPTION OF DRAWINGS

The accompanying drawings, which are incorporated in and constitute a part of this specification, illustrate the disclosed embodiments and together with the description, serve to explain the principles of the various aspects of the disclosed embodiments. In the drawings.

Figure 1:
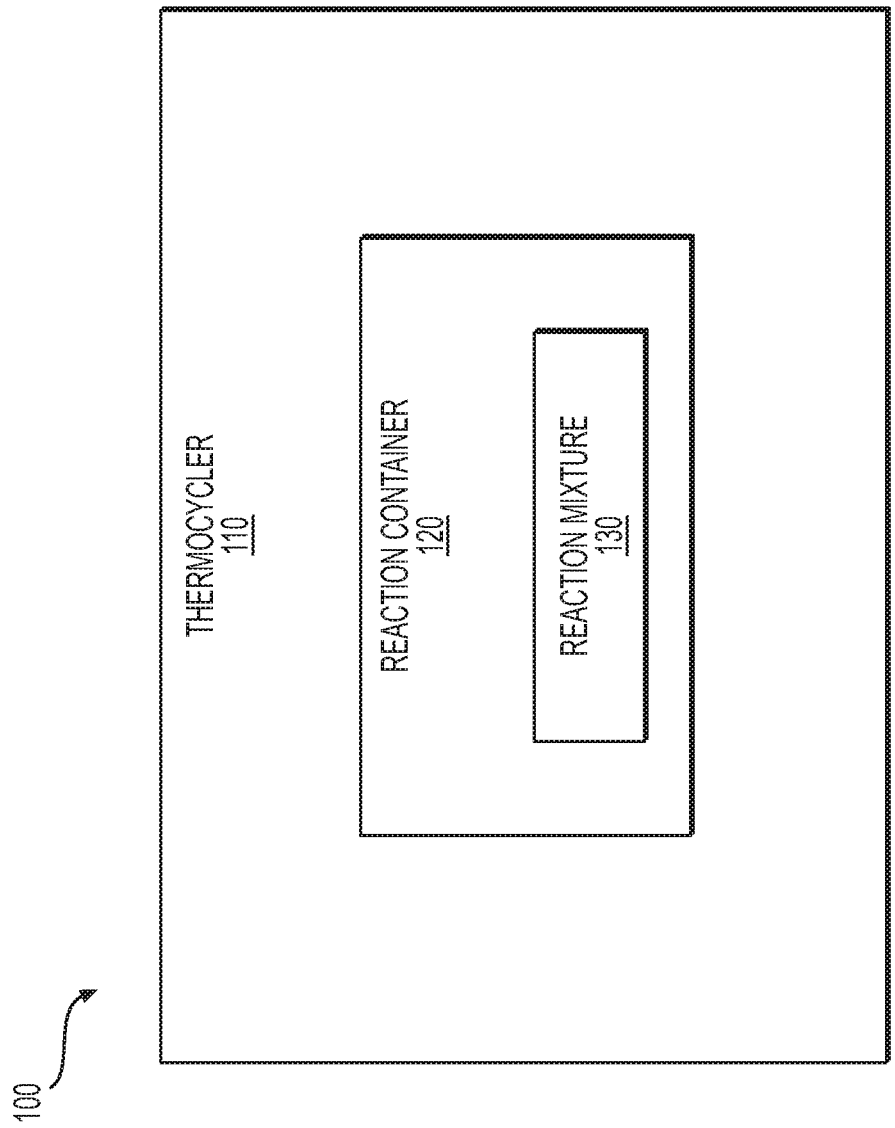
FIG. 1 illustrates a system for amplifying nucleic acid in accordance with exemplary embodiments of the present disclosure.

It is to be understood that both the foregoing general description and the following detailed description are exemplary and explanatory only and are not restrictive of the disclosed embodiments, as claimed.

DESCRIPTION OF EXEMPLARY EMBODIMENTS

Reference will now be made to certain embodiments consistent with the present disclosure, examples of which are illustrated in the accompanying drawings. Wherever possible, the same reference numbers are used throughout the drawings to refer to the same or like parts.

The present disclosure describes methods for amplifying nucleic acid, comprising two steps: a first step of preparing a reaction mixture comprising the target nucleic acid and a second step of processing the reaction mixture in a thermocycler. During a first phase of the processing step, the thermocycler may be configured to heat the reaction mixture to a first temperature and cool the reaction mixture to a second temperature repeatedly for a first plurality of cycles. During a second phase of the processing step, the thermocycler may heat the reaction mixture to a third temperature and cool the reaction mixture to a fourth temperature repeatedly for a second plurality of cycles. The disclosed methods may be employed for nucleic acid amplification, detection, and quantification in clinical and/or research settings.

For the purposes of this disclosure it will be assumed that the target nucleic acid for amplification, detection, and/or quantification is DNA. However, as described herein, this disclosure is not limited to DNA and may apply to or be included in the amplification of other nucleic acids, such as cDNA or RNA. A thermal cycle of a PCR process may, for example, comprise DNA template denaturation (separation of the double strands), primer annealing, and primer extension. DNA denaturation is typically set at a high temperature, for example, from 90° C. to 100° C., at which the double-stranded DNA template is melted and the DNA polymerase, for example, Taq DNA polymerase, can be activated. Primers in a PCR process, for example, may include a forward primer and a reverse primer, which anneal or adhere to their respective DNA template strand at the beginning and ending locations of the target DNA sequence to be amplified. The melting temperature of a primer can be defined as the temperature at which 50% of the primers form a stable double-stranded helix with the target DNA and the other 50% exist as single-stranded DNA. The melting temperatures of the primers set the limit for the annealing temperature, which is set, for example, the same as or about 5° C. to 10° C. below the melting temperatures. The length of primers is generally 15 to 25 nucleotides with a melting temperature approximately ranging from 55° C. to 65° C. Primer extension is carried out by DNA polymerase, which binds to the primer-template hybrid and begins the synthesis of the new DNA strand. For the DNA polymerase to initiate and/or perform DNA synthesis, primer extension is generally set at an optimum temperature, for example, ranging from 70° C. to 80° C. If the temperatures for annealing and extension are similar, these two stages can be combined. In general, each thermal cycle of the PCR process may double the amount of the target DNA or template DNA in the reaction. Therefore, 10 cycles may, for example, multiply the target DNA by approximately a factor of 1000. The accumulated amplified target DNA is typically referred to as the PCR product or the amplicon.

The time for each thermal cycle of a PCR process may depend on different conditions, such as the temperatures, the enzymatic activity of the DNA polymerase, and the sequences of the target DNA and primers, and may be notably limited by the ramp rate of the thermocycler. Most thermocyclers designed for PCR applications currently use Peltier thermoelectric heat pumps to conduct precise temperature control and rapid heating and cooling of the reaction mixture. Other types of thermocyclers may use solid state heater and forced-air cooling, such as the SmartCycler® System of Cepheid. In some embodiments, in vitro diagnostic instruments that can perform thermocyling may be used for a PCR process, such as the Applied Biosystems® 7500 Fast Dx Real-Time PCR Instrument. The ramping rate of heating or cooling of the thermocyclers or instruments generally may range from 1° C./second to 10° C./second. For example, to perform thermocycling between a denaturation temperature of 95° C. and an annealing temperature of 65° C., a thermocycler having a ramp rate of about 5° C./second may require 12 seconds to ramp the temperature from 65° C. to 95° C. and back to 65° C. The total amount of time required for transition temperatures and hold temperatures in a 45-cycle PCR process may add up to about 45 minutes. Thus, to reduce the time of the PCR process, the inventors have recognized that increasing the melting temperature of the primers and thus the annealing temperature of the primers may reduce the temperature-transition time of each thermal cycle, and therefore reduce the time for the PCR process. Exemplary methods for amplifying nucleic acid in accordance with present disclosure may use primers that have high melting temperatures and annealing temperature.

Exemplary methods for amplifying nucleic acid in accordance with present disclosure may be used for real-time PCR or quantitative PCR. However, as disclosed herein, this disclosure is not limited to real-time PCR or quantitative PCR. Real-time PCR allows accurate quantification of the starting amounts of target DNA, cDNA, and RNA. Typically in real-time PCR, fluorescence dyes or fluorescence probes are included in the reaction mixture and emit fluorescence signals upon excitation during each thermal cycle. The amount of fluorescence or the fluorescence intensity from the reaction mixture is measured and generally proportional to the amount of the PCR product or the amplicon. Either fluorescent dyes that bind to double-stranded DNA or fluorescently labeled probes that specifically bind to the target DNA may be used in real-time PCR, such as, for example, SYBR Green®, TaqMan® probes, and FRET probes. For the purposes of illustrating the exemplary embodiments of the present disclosure, it will be assumed that TaqMan® probes are used in real-time PCR. However, as disclosed herein, this disclosure is not limited to real-time PCR using TaqMan® probes.

TaqMan® probes, for example, are sequence-specific oligonucleotide probes carrying a reporter molecule and a quencher molecule. TaqMan® probes rely on the 5'-3' exonuclease activity of Taq DNA polymerase to cleave the probe during synthesis of the new DNA strand. The reporter molecule is covalently attached at the 5' end of the probe and the quencher molecule is covalently attached at the 3' end. The length of the probe is designed such that as long as the reporter molecule and the quencher molecule are in close proximity, the quencher molecule quenches the fluorescence emitted by the reporter molecule upon excitation via Fluorescence Resonance Energy Transfer. During the primer annealing and/or extension stage of each PCR thermal cycle, the probe that is annealed or adhered to the target DNA sequence is cleaved by the 5'-3' exonuclease activity of Taq DNA polymerase, separating the reporter and the quencher molecules. This separation results in detectable fluorescence signals from the reporter molecule that can be used for real-time detection of the amplicon.

Taq DNA polymerase, for example, has an extension rate of about 100 base pair of DNA per second at a temperature around 72° C. The extension rate can be reduced by about 2 to 5 times if the Taq DNA polymerase has to cleave the probe by its 5'-3' exonuclease activity during the enzymatic extension of the PCR process. To reduce the time of the PCR process, the inventors have also recognized that it may be advantageous to develop a two-phase PCR process. During the first phase of the two-phase PCR process, probes may not anneal to target DNA during the annealing stage, and during the second phase, the probes may anneal to the to target DNA during the annealing stage. In such situations, during the first phase, the speed of Taq DNA polymerase for primer extension may be significantly improved, for example, by about 2 to 5 times, reducing the time for thermal cycles of the first phase and thus the total amount of time for the PCR process. During the second phase, the probes may anneal to the target DNA and be cleaved by Taq DNA polymerase to emit fluorescence signals proportional to the amount of the amplicon. In some embodiments, the fluorescence signals measured during the second phase may be used for determining a threshold cycle ($C_t$), at which the fluorescence signal, for example, crosses a user-defined threshold. In some embodiments, the threshold cycle ($C_t$) may be used for either absolute quantification or relative quantification of the amount of target DNA in the tested sample.

As shown in FIG. 1, exemplary embodiments of a system 100 for amplifying nucleic acid in accordance with the present disclosure may comprise a thermocycler 110 and a reaction container 120. Reaction container 120 may hold a reaction mixture 130 and be placed in thermocycler 110. In preferred embodiments, reaction container 120 may be thermally conductive. Thermocycler 110 may comprise at least one of a processor, a device for holding reaction container 120, a heating element, a cooling element, a temperature sensor, an input unit, a detection and/or quantification unit, and an output unit. In some embodiments, thermocycler 110 may be configured to heat and cool reaction mixture 130 at predetermined ramp rates ranging from 1° C./second to 10° C./second under the control of the processor or a computer operatively connected to thermocycler 110. In exemplary embodiments, reaction mixture 130 may have a reaction volume ranging from 5 µl to 50 µl. In preferred embodiments, reaction mixture 130 may comprise a buffer solution, dNTPs or nucleoside triphosphates, primers, DNA polymerase, and the target nucleic acid. In some embodiments, reaction mixture 120 may be contained in one reaction container 120 throughout the two-phase PCR process. In other embodiments, reaction mixture 120 may be transferred among at least one reaction container 120 during the two-phase PCR process.

Figure 2:
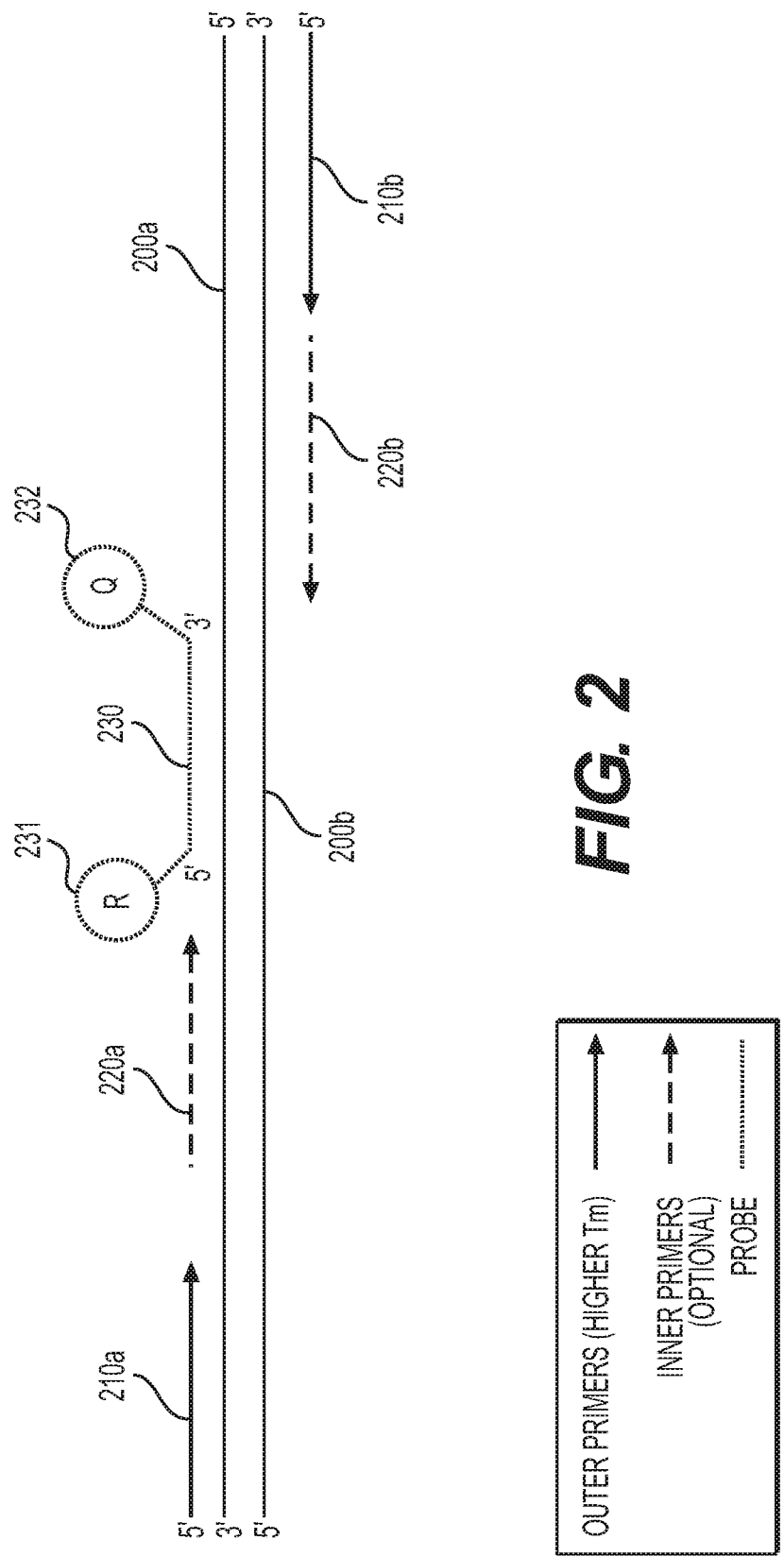
FIG. 2 illustrates methods for amplifying nucleic acid in accordance with exemplary embodiments of the present disclosure.

In some embodiments, methods for amplifying nucleic acid in accordance with present disclosure may include using primers that have high melting temperatures to reduce the temperature-transition time. As shown in FIG. 2, target DNA may comprise two template stands, 200a and 200b: one is a sense strand and the other is an antisense strand. Also shown are a first "outer" primer set 210a and 210b (referred to collectively as primer set 210), and an optional second "inner" primer set 220a and 220b (referred to collectively as primer set 220). A primer set 210 that has high melting temperatures may comprise a forward primer 210a and a reverse primer 210b. In exemplary embodiments, the melting temperatures of forward primer 210a and reverse primer 210b may range from 70° C. to 80° C. The melting temperatures of forward primer 210a and reverse primer 210b may differ within about 0° C. to 5° C.

In some embodiments, methods for amplifying target DNA may comprise processing reaction mixture 130 comprising the target DNA and primers in thermocycler 110 in a two-phase PCR process. During the first phase of the PCR process, the annealing temperature is designed to be higher than the melting temperature of the probes such that the probes may not anneal to the to target DNA and the speed of Taq DNA polymerase for primer extension may be increased, for example, by about 2 to 5 times over its typical extension rate. During the second phase, the annealing temperature is designed to be approximately the same as or below the melting temperature of the probes such that the probes may anneal to the target DNA and be cleaved by Taq DNA polymerase to emit fluorescence signals for detection and/or quantification of the amplicon. In some embodiments, the annealing temperature for the first phase may be, for example, the same as or about 0° C. to 5° C. below the melting temperatures of primers 210a and 210b so that the temperature-transition time of each thermal cycle in the first phase may be less than a typical PCR process. In exemplary embodiments, the two-phase PCR process reduces the time for the thermal cycles of the first phase and thus the total amount of time for the PCR process.

In some embodiments, in each of the thermal cycle during a first phase of the PCR process, thermocycler 110 may be configured to heat reaction mixture 130 to a first temperature, for example, about 90° C. to 100° C., to denature the target DNA into the two template strands 200a and 200b. In some embodiments, thermocycler 110 may maintain reaction mixture 130 at the first temperature for a predetermined period of time, for example, for about 1 to 10 seconds. In some embodiments, thermocycler 110 then may be configured to cool reaction mixture 130 from the first temperature to a second temperature, for example, the annealing temperature of primer set 210. In some embodiments, the annealing temperature is approximately the same as or slightly below the melting temperatures of primer set 210. In some embodiments, thermocycler 110 may maintain reaction mixture 130 at the second temperature for a predetermined period of time, for example, for about 2 to 20 seconds, 2 to 30 seconds, or 2 to 40 seconds. In some embodiments, thermocycler 110 may repeat the thermal cycle between the first and second temperatures for a first number of times, for example, for about 10 to 35 times.

In each of the thermal cycle during a second phase of the PCR process, thermocycler 110 may be configured to heat reaction mixture 130 to a third temperature, for example, about 80° C. to 100° C., to denature the target DNA into template strands 200a and 200b. In some embodiments, the third temperature may be determined by the sequence and/or melting temperature of the amplicon. In some embodiments, the third temperature is approximately the same as or within a few degrees of the first temperature. In some embodiments, thermocycler 110 may maintain reaction mixture 130 at the third temperature for a predetermined period of time, for example, for about 1 to 10 seconds. Thermocycler 110 then may be configured to cool reaction mixture 130 from the third temperature to a fourth temperature. In some embodiments, the fourth temperature may be lower than the annealing temperature and/or the melting temperatures of primer set 210, for example, the fourth temperature may lower than melting temperatures of primer set 210 by about 5° C. to 20° C. In some embodiments, thermocycler 110 may maintain reaction mixture 130 at the fourth temperature for a predetermined period of time, for example, for about 2 to 20 seconds, 2 to 30 seconds, or 2 to 40 seconds. In some embodiments, thermocycler 110 may repeat the thermal cycle between the third and fourth temperatures for a second number of times, for example, ranging from 10 to 30 times.

In some embodiments, methods for amplifying nucleic acid in accordance with present disclosure may include using probes in the second phase of the PCR process to generate fluorescent signals for amplifying, detecting, and/ or quantifying target DNA. As shown in FIG. 2, reaction mixture 130 may comprise probe 230, attached with a reporter molecule 231 at one end and a quencher molecule 232 at the other end. In some embodiments, the melting temperature of probe 230 may be lower than that of primer set 210, for example, the melting temperature of probe 230 may be 5° C. to 10° C. lower than the melting temperatures and/or the annealing temperatures of forward primer 210a and/or reverse primer 210b. In some embodiments, the melting temperature of probe 230 may be lower than the second temperature of the first phase of the PCR process. In some embodiments, the melting temperature of probe 230 may range from 55° C. to 70° C. In some embodiments, the concentration of probe 230 in reaction mixture 130 may range from 0.1 µM to 0.4 µM, from 0.1 µM to 0.6 µM, from 0.1 µM to 0.8 µM, or from 0.1 µM to 1 µM. In some embodiments, more than one type of probes 230 may be included in reaction mixture 130 for the detection, amplification, and/or quantification of at least one target DNA sequence.

Figure 3:
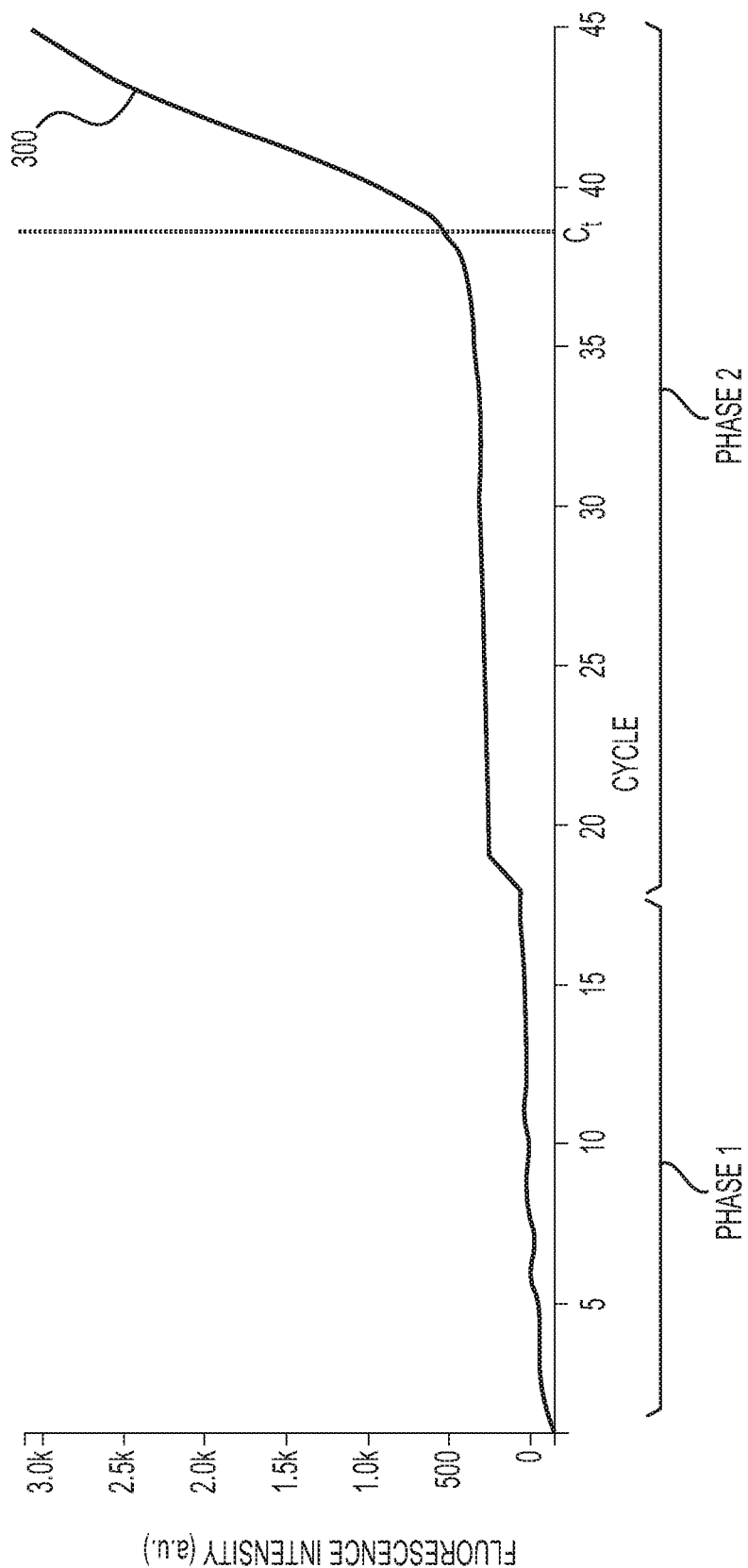
FIG. 3 illustrates an exemplary data set of a PCR process in accordance with exemplary embodiments of the present disclosure.

In some embodiments, since the melting temperature of probe 230 is lower than that of primers 210a and 210b, and/or the second temperature of the first phase of the PCR process, during primer annealing of the first phase, probe 230 may not anneal to the target DNA and thus may not generate fluorescence signals. In some embodiments, during the first phase of the PCR process, as shown in FIG. 3, fluorescence signals from reporter molecule 231 of probe 230 may be limited or negligible. In some embodiments, the melting temperature of probe 230 may, for example, be approximately the same as or about 1° C. to 10° C. above the fourth temperature of the second phase. In other embodiments, the melting temperature of probe 230 may be between the second temperature of the first phase of the PCR process and the fourth temperature of the second phase. In some embodiments, the melting temperature of probe 230 may be between the melting temperatures or annealing temperature of primers 210a and 210b and the fourth temperature of the second phase. In some embodiments, probe 230 may anneal or adhere to the target DNA and/or the amplified DNA produced during the first phase and be degraded by Taq DNA polymerase during the second phase of the PCR process. For example, during the second phase, as Taq DNA polymerase extends primers 210a and 210b and synthesizes the new DNA strand, it cleaves and degrades probe 230 that has annealed to the target DNA by its 5'-3' exonuclease activity, separating reporter molecule 231 and quencher molecule 232 and thus relieving the quenching effect, which may allow reporter molecule 231 to emit fluorescence. In some embodiments, as shown in FIG. 3, thermocycler 110 may be configured to have a fluorescence detection and/or quantification unit that measures fluorescence signals or fluorescence intensity from reaction mixture 130 during the annealing and/or extension stage of the second phase of the PCR process. In some embodiments, more than one type of probes 230 may anneal to the same target DNA during the annealing and/or extension stage of the second phase of the two-phase PCR process.

In some embodiments, since probe 230 is not annealed to target DNA during the annealing stage of the first phase, the speed of Taq DNA polymerase for primer extension may be significantly improved, reducing the time for thermal cycles of the first phase and thus the time for the total PCR process. In some embodiments, the amplicon produced during the first phase may be further amplified during the second phase, as shown in FIG. 3, and fluorescence signals measured during the second phase may be used for determining a threshold cycle ($C_t$), at which the fluorescence amplification plot 300, for example, crosses a user-defined threshold. In some embodiments, the threshold cycle ($C_t$) may be used for either detection or quantification of the amount of target DNA in the tested sample.

In some embodiments, the fourth temperature of each of the thermal cycle during the second phase of the PCR process may decrease progressively from the second temperature of the first phase of the PCR process. For example, in each thermal cycle of the second phase, thermocycler 110 may be configured to heat reaction mixture 130 to the third temperature to denature the target DNA into template strands 200a and 200b, maintain reaction mixture 130 at the third temperature for a predetermined period of time, and cool reaction mixture 130 from the third temperature to the fourth temperature that is progressively lower than the second temperature of the first phase. In some embodiments, the fourth temperature may gradually decrease to become lower than the annealing temperature and/or the melting temperatures of primer set 210 over a number of thermal cycles, for example, the fourth temperature may become lower than the melting temperatures of primer set 210 by about 5° C. to 20° C. after a predetermined number of thermal cycles.

One of the major technical difficulties with PCR is to specifically amplify the target DNA. The primer annealing stage is critical to achieve high PCR specificity. Annealing of primers to the template DNA with high specificity leads to high yields of specific target DNA amplification and thus increases the sensitivity of the amplification reaction. However, due to the typically high primer concentration in the reaction mixture, primers will also nonspecifically anneal to non-complementary DNA sequences with mismatches, which may lead to amplification of nonspecific DNA sequences and primer-dimers. Competition in the amplification reaction between these nonspecific sequences and the desired target DNA may reduce the yield and the sensitivity of the PCR process. One of the advantages of the methods in accordance with the embodiments of the present disclosure is to improve the specificity of the PCR process by using primers having high melting temperatures.

In some embodiments, in the first phase of the PCR process, primers 210a and 210b anneal to the template DNA at a high annealing temperature, for example, approximately the same as or about 5° C. to 10° C. below the melting temperatures of the primer set 210. The first phase of the two-phase PCR process may limit or eliminate nonspecific binding of primers 210a and 210b to the template DNA and/or formation of primer-dimers. Thus, the DNA sequence amplified during the first phase is mostly likely the target DNA, which may be further amplified during the second phase of the PCR process, and may advantageously compete with the nonspecific sequences to which primers 210a and 210b may bind at the lower annealing temperatures during the second phase.

In some embodiments, the melting temperatures of primers 210a and 210b may be designed and modulated. For example, the melting temperature of a primer may depend on the length of the primer. In some embodiments, the lengths of primers 210a and 210b may range from 18 to 35 base pairs, which may, for example, results in melting temperatures ranging from 60° C. to 80° C. In some embodiments, adjusting the GC content of the primers may modulate their melting temperatures. For example, in some embodiments, the GC content of primers 210a and 210b may range from 40% to 60%, which may, for example, results in melting temperatures ranging from 60° C. to 80°

C. In some embodiments, the annealing temperature may be slightly above the melting temperatures, for example, by about 5° C. to 10° C. A number of conditions may affect the melting temperatures of the primers and thus the annealing temperature during the PCR process. For example, at least one the following conditions may affect the melting temperature and/or the annealing temperature of the primers: the concentrations of primers, dNTP, $Mg^{2+}$, $K^+$, $Mn^{2+}$, and other cation components in the reaction mixture, additives in the reaction mixture, such as dimethyl sulfoxide (DMSO), bovine serum albumin (BSA), and glycerol, sequences of the target DNA and primers, the enzymatic activity of the DNA polymerase used in the reaction, and the performance of the thermocycler. In some embodiments, the melting temperature and the annealing temperature of the primers may be designed, analyzed, and optimized based on the PCR conditions and may vary for different amplification reactions and/or applications. In some embodiments, the melting temperature and the annealing temperature of the primers may be experimentally measured. In some embodiments, the melting temperature and the annealing temperature of the primers may be theoretically calculated based on thermodynamic models. In some embodiments, primers may be designed and optimized using software tools, such as BLAST, Oligo Analyzer, OligoPerfect Designer, or $T_m$ Calculator by Life Technologies. In some embodiments, the melting temperature and the annealing temperature of the primers and/or the amplicon may vary, for example, for about 1° C. to 10° C., depending on the method, model, or tool used for measuring and/or calculating the melting temperature.

In some embodiments, the melting temperatures of primers 210a and 210b may be designed to increase during the PCR process. For example, forward primer 210a and reverse primer 210b may be designed to have extra A, T, G, and/or C nucleotides added to their 3' end, which may not be complementary to the target DNA. In some embodiments, the number of the additional nucleotides may range from 1 to 10 nucleotides. During the first phase of the PCR process, the additional A, T, G, and/or C nucleotides may not anneal to the target DNA for an initial number of thermal cycles, for example, about 1 to 10 thermal cycles. In some embodiments, in the subsequent thermal cycles, as the complimentary DNA strand is being made, the additional A, T, G, and/or C nucleotides may become incorporated into the sequence of the amplicon. In some embodiments, in the subsequent thermal cycles of the first phase and/or second phase of the PCR process, these additional A, T, G, and/or C bases may become part of the sequence of the amplicon that has been previously made and continue to become incorporated into the new DNA strands or amplicon being made. In such situations, using the primers designed with additional mismatching or non-complementary A, T, G, and/or C nucleotides may increase the melting temperatures and thus the annealing temperature of the primers to the target DNA during the PCR process. The complementary base pairing between G and C nucleotides forms three hydrogen bonds whereas the complementary base pairing between A and T nucleotides forms two hydrogen bonds, resulting in stronger interaction between the G and C nucleotides than the A and T nucleotides. Thus, in some embodiments, primers designed with the additional nucleotides may include more G and/or C nucleotides than A and/or T nucleotides to increase the melting temperature and annealing temperature of the primers. In some embodiments, A and/or T nucleotides among the additional nucleotides added to the primers may limit or prevent formation of primer dimers. Similar to the above-discussed embodiments, increasing the melting temperatures and annealing temperature reduces the temperature difference between the denaturation temperature and the annealing temperature, and reduces the transition time between these temperatures and thus the time of the PCR process.

In some embodiments, locked nucleic acid (LNA) may be used in place of or in combination with DNA as primers. LNA is modified RNA with an extra bridge connecting the 2' oxygen and 4' carbon of the ribose. The conformation of the locked ribose enhances base stacking and backbone pre-organization, which may significantly increase the melting temperature of oligonucleotides. In some embodiments, primers 210a and 210b may comprise both DNA nucleotides and LNA nucleotides, whose contents may be adjusted and designed to achieve a desired melting temperature. In other embodiments, primers 210a and 210b comprising LNA nucleotides may have better specificity to target DNA sequence than those comprising only DNA nucleotides.

In some embodiments, peptide nucleic acid (PNA) may be used in place of or in combination with DNA as primers. PNA oligomer may have greater specificity in binding to complementary DNA sequence than DNA oligomers and a PNA/DNA base mismatch may be more destabilizing than a similar mismatch in a DNA/DNA duplex. Since the backbone of PNA contains no charged phosphate groups, the binding between PNA/DNA strands is stronger than between DNA/DNA strands due to the lack of electrostatic repulsion between the backbones. In some embodiments, primers 210a and 210b may comprise a PNA oligomer, whose length may be adjusted and designed to achieve a desired melting temperature. In some embodiments, primers 210a and 210b comprising PNA oligomers may have stronger binding to target DNA, and thus higher melting temperature. In some embodiments, primers 210a and 210b comprising PNA may have better specificity to target DNA sequence than primers comprising DNA.

In some embodiments, primers 210a and 210b may be designed to have mismatched based pairs that do not perfectly match to one of their target sequences. For example, primers 210a and 210b may have, for example, about 1 to 10 mismatched base pairs to one of the target DNA sequences. In such situations, primers 210a and 210b may anneal and/or bind to more than one target DNA sequences. In some embodiments, the mismatched base pairs of primers 210a and 210b may vary and different primers 210a and 210b with different mismatched based pairs may be included in reaction mixture 130 based on the intended target DNA sequences. In exemplary embodiments, primers 210a and 210b may allow amplification of mutated, genetically modified, or closely related DNA or RNA sequences.

In some embodiments, the second phase of the PCR process may be optional and the melting temperature of probe 230 may be approximately the same as the melting temperatures or annealing temperature of primers 210a and 210b. In some embodiments, probe 230 may anneal or adhere to the target DNA and be degraded by Taq DNA polymerase during the first phase of the PCR process so that fluorescence signals may be detected and used for detection and/or quantification of target DNA during the first phase.

In some embodiments, primers 210a and 210b may have higher primer annealing probability and thus amplification efficiency during the second phase than during the first phase of the PCR process. In some embodiments, primers 210a and 210b may have reduced annealing specificity to the target DNA during the second phase than during the first phase of the PCR process. Therefore, in some embodiments, another set of optional primers 220 that have lower melting temperatures than primers 210a and 210b may be included in reaction mixture 130. As shown in FIG. 2, optional primer set 220 may comprise a forward primer 220a and a reverse primer 220b. For the illustration of exemplary embodiments of this disclosure, primer set 210 may be referred to as the outer primers and primer set 220 may be referred to as the inner primers. In some embodiments, the melting temperatures of primers 220a and 220b may be lower than those of primers 210a and 210b by about 5° C. to 20° C. In some embodiments, the melting temperatures of forward primer 220a and reverse primer 220b may range from 55° C. to 70° C. and may differ within about 0° C. to 5° C. In some embodiments, the concentration of primers 210a and 210b in reaction mixture may range from 0.2 µM to 6 µM. In some embodiments, the concentration of primers 220a and 220b in reaction mixture may range from 0.1 µM to 3 µM.

In some embodiments, in each of the thermal cycle during the second phase of the PCR process, the melting temperatures of primer set 220 may be approximately the same as or slightly above the fourth temperature, for example, by about 5° C. to 10° C. Similar to the exemplary embodiments disclosed above, in some embodiments, thermocycler 110 may maintain reaction mixture 130 at the fourth temperature for a predetermined period of time and may repeat the thermal cycle between the third and fourth temperatures for a predetermined number of times. In some embodiments, primers 220a and 220b may anneal to the target DNA during the annealing stage of the second phase of the PCR.

In exemplary embodiments, primers 210a and 210b may anneal to the target DNA during the annealing stage of the first phase of the PCR process and may also anneal to the target DNA during the annealing stage of the second phase of the PCR. In exemplary embodiments, primers 220a and 220b may not anneal to the target DNA during the annealing stage of the first phase of the PCR. For example, during the first phase, primer annealing is carried out at the second temperature, which may be approximately the melting temperatures and/or the annealing temperature of primers 210a and 210b. Thus, primers 210a and 210b may anneal to the target DNA while primers 220a and 220b, whose melting temperatures are lower than primers 210a and 210b, may not anneal to the target DNA. During the second phase, for example, primer annealing is carried out at the fourth temperature, which may be approximately the melting temperatures and/or the annealing temperature of primers 220a and 220b. Thus, during the second phase, both primers 220a and 220b and primers 210a and 210b may anneal to the target DNA. In some embodiments, primers 210a and 210b may have lower specificity to the target DNA sequence during the second phase of the PCR than during the first phase. In some embodiments, primers 220a and 220b may have higher binding specificity to target DNA than primers 210a and 210b during the second phase of the PCR process.

Figure 4:
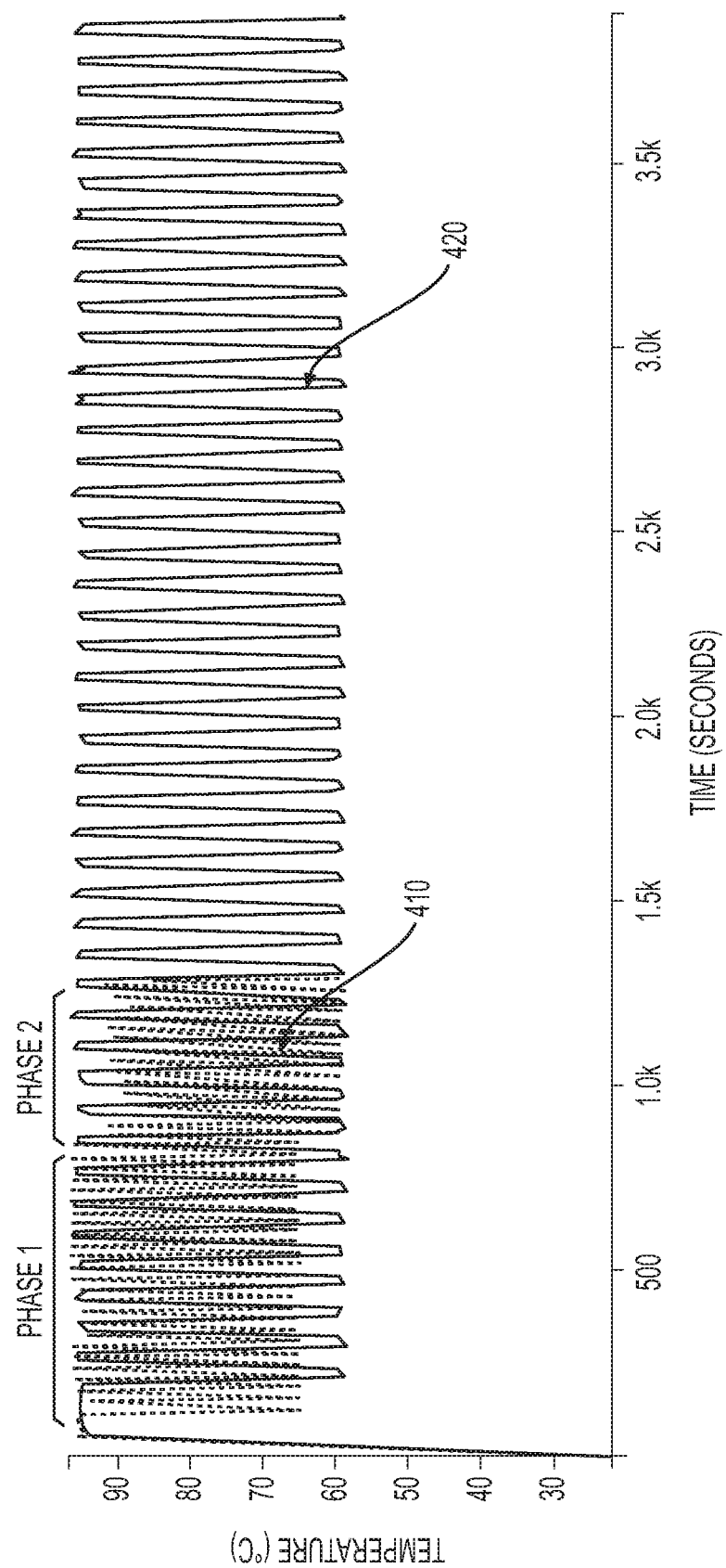
FIG. 4 illustrates exemplary thermal profiles of PCR processes in accordance with exemplary embodiments of the present disclosure.

In some embodiments, each of the thermal cycle during the first phase of the PCR process may take about 2 to 50 seconds, and each of the thermal cycle during the second phase of the PCR process may take about 2 to 50 seconds. In some embodiments, the thermal cycles during the first phase may be repeated for about 10 to 30 times, and the thermal cycles during the second phase may be repeated for about 10 to 30 times. In some embodiments, the time for the first phase of the PCR process may last for about 5 to 30 minutes, and the time for the second phase of the PCR process may last for about 5 to 30 minutes. In some embodiments, the total time for the two-phase PCR process may last for about 10 to 45 minutes, 15 to 45 minutes, or 15 to 60 minutes. In exemplary embodiments, the time for the two-phase PCR may be significantly shorter than a typical PCR process. For example, as shown in FIG. 4, the thermoprofile of an exemplary two-phase PCR process 410 may last for about 1300 seconds or 22 minutes while the thermoprofile of an exemplary typical PCR process 420 may last for about 3800 seconds or 63 minutes.

In some embodiments, reaction mixture 130 may comprise more than one kind of primer set 210. For example, reaction mixture 130 may comprise three kinds of primer set 210 and each primer set 210 may be specific to a target DNA sequence. In such situations, three kinds of primer set 210 may be designed to amplify and/or detect three kinds of target DNA sequences during the first phase of the PCR process. In some embodiments, reaction mixture 130 may comprise more than one kind of primer set 220. For example, reaction mixture 130 may comprise three kinds of primer set 220 and each primer set 220 is specific to a target DNA sequence. In such situations, three kinds of primer set 220 may be designed to amplify and/or detect three kinds of target DNA sequences during the second phase of the PCR process. In some embodiments, primer set 210 and primer set 220 may be paired and both may be specific to the same target DNA sequence. For example, reaction mixture 130 may comprise three pairs of primer set 210 and primer set 220 designed to amplify and/or detect three kinds of target DNA sequences during the PCR process.

Exemplary embodiments of the methods for amplifying nucleic acid in accordance with the present disclosure may comprise initial and/or finishing steps. The initial steps may comprise heating reaction mixture 130 to intermediate temperatures, for example, about 40° C. to 95° C., and holding reaction mixture 130 at least at one of the intermediate temperatures for a predetermined period of time, for example, for about 2 seconds to 15 minutes. In some embodiments, the finishing steps may comprise cooling the reaction mixture to intermediate temperatures, for example, about 4° C. to 40° C., and holding the reaction mixture at least at one of the intermediate temperatures for a predetermined period of time, for example, about a few seconds to a few hours.

In some embodiments, the melting and annealing temperatures, number of thermal cycles, and time periods for holding each temperature of each of the two phases of the PCR process, may vary and depend on a variety of conditions, which may be one or more selected from the following: concentrations of $Na^+$, $Mg^{2+}Mn^{2+}$, $K^+$, buffer components and types, water purity, lengths, sequences, and modifications of primers, efficiency of fluorescence dyes, PCR types, the type and enzymatic activity of the DNA polymerase types, such as fast speed DNA polymerase and high-fidelity DNA polymerase with proofreading capability, the sequences of the target DNA and primers, the capability of the thermocycler, and other optimization steps.

EXAMPLES OF METHODS FOR AMPLIFYING NUCLEIC ACID IN ACCORDANCE WITH EMBODIMENTS OF THE PRESENT DISCLOSURE

Example 1

Amplification and Quantification of *Streptococcus pyogenes* or Group A *Streptococcus* (GAS) DNA with Only Outer Primers and Both Outer Primers and Inner Primers Two-phase PCR was performed to two series of samples having *Streptococcus pyogenes* or GAS DNA. Each series had 3 samples, each sample having one of 3 diluted concentrations of GAS DNA starting from 1 pg/reaction to 100 pg/reaction or from 500 copies to 5000 copies respectively. The first series of 3 samples had outer primers (primers 210a and 210b) at a concentration of 3 µM and no inner primers. The second series of 3 samples had outer primers at a concentration of 3 µM and inner primers (primers 220a and 220b) at a concentration of 0.6 µM. The melting temperatures of the outer primers were about 72° C. and the melting temperatures of the inner primers were about 60° C. The total volume of each sample was 25 µL. The thermocycling profile of the two-phase PCR process for all of the samples was the following: initial steps: 40° C. for 2 seconds, 95° C. for 60 seconds; first phase: 18 cycles between 95° C. for 2 seconds and 72° C. for 2 seconds; second phase: 27 cycles between 90° C. for 2 seconds and 65° C. for 2 seconds. The amount of time for the two-phase PCR was about 4 minutes of assay time, or about 25 minutes total including the time for changing the temperatures, significantly less than that of a typical PCR process.

Each sample had probes 230 at a concentration of 0.4 µM. The melting temperatures of the probes was about 70° C. During the second phase of the PCR process, the probes annealed to the target GAS DNA and was cleaved by Taq DNA polymerase such that fluorescence signal 300 from the probes was emitted and detected. A $C_t$ value was determined based on the detected fluorescence signal for each sample during the second phase when the fluorescence detection and/or quantification unit of thermocycler 110 was in operation, as shown in Table 1. The results show that the two-phase PCR process can detect low concentrations of target DNA using only outer primers or both outer primers and inner primers within about 25 minutes.

TABLE 1

$C_t$ values of samples having diluted concentrations of Group A Streptococcus (GAS) DNA with only outer primers and both outer primers and inner primers.

| DNA Concentration (per reaction) | $C_t$ (Outer primers only) | $C_t$ (Outer primers and inner primers) |
|---|---|---|
| 100 pg = 50,000 copies | 31.8 | 32.1 |
| 10 pg = 5000 copies | 35.0 | 35.9 |
| 1 pg = 500 copies | 37.0 | 38.6 |

Example 2

Amplification and Detection of Influenza A, Influenza B, and Human Respiratory Syncytial Virus (RSV) RNA Two-phase PCR was performed to a series of 6 samples: samples 1 and 2 had Influenza A RNA, samples 3 and 4 had Influenza B RNA, and samples 4 and 5 had Human respiratory syncytial virus (RSV) RNA. Each sample included outer primers (primers 210a and 210b) at a concentration of 2 µM. No inner primers (primers 220a and 220b) were included. Three sets of outer primers and probes were designed for the three target virus RNAs in the samples. For example, a first set of outer primers and 4 probes were designed for amplifying Influenza A RNA, a second set of outer primers and 2 probes were designed for amplifying Influenza B RNA, and a third set of outer primers and 3 probes were designed for RSV RNA. Each sample included all of the three sets of outer primers and probes. Each of the first set of 4 probes was at a concentration of 0.4 µM and the total concentration of the 4 probes was 1.6 µM. Each of the second set of 2 probes was at a concentration of 0.3 µM and the total concentration of the 2 probes was 0.6 µM. Each of the third set of 3 probes was at a concentration of 0.4 µM and the total concentration of the 3 probes was 1.2 µM. The first set of probes were attached with FAM™ dyes as the reporter, the second set of probes were attached with Dragonfly Orange™ dyes as the reporter, and the third set of probes were attached with Texas Red® dyes as the reporter. Each reporter had a different fluorescence emission spectrum. The melting temperatures of the outer primers were about 71° C. to 82° C. and the melting temperatures of the probes were about 68° C. to 85° C. The total volume of each sample was 25 µL. The thermocycling profile of the two-phase PCR process for all of the samples was the following: initial steps: 50° C. for 600 seconds, 95° C. for 120 seconds; first phase: 15 cycles between 90° C. for 5 seconds and 70° C. for 5 seconds; second phase: 30 cycles between 90° C. for 5 seconds and 64° C. for 30 seconds. The amount of time for the two-phase PCR was about 32 minutes of assay time, or about 50 minutes total including the time for changing the temperatures. A typical PCR process for a traditional Flu/RSV assay of these samples took about 110 minutes.

The detection of fluorescence signal 300 was performed for each of the probes similarly to the first example. A $C_t$ value was determined based on the detected fluorescence signal for each sample during the second phase when the fluorescence detection and/or quantification unit of thermocycler 110 was in operation, as shown in Table 2. The results show that the two-phase PCR process can detect low concentrations of viral RNAs using only outer primers within about 50 minutes, and that the two-phase PCR process according to exemplary embodiments of the present disclosure is much faster than the typical PCR process for viral RNA detection and/or quantification. The $C_t$ values obtained from the two-phase PCR process can then be used to determine the amount of target viral RNA and/or DNA in the samples by comparing them to a standard curve of the $C_t$ values of a standard sample.

TABLE 2

$C_t$ values of samples having Influenza A, Influenza B, and Human respiratory syncytial virus (RSV) RNA.

| Sample Tested | FAM ™ $C_t$ (Influenza A) | DFO ™ $C_t$ (Influenza B) | TxR ® $C_t$ (RSV) |
|---|---|---|---|
| Sample 1: Influenza A | 21.7 | | |
| Sample 2: Influenza A | 21.3 | | |
| Sample 3: Influenza B | | 21.0 | |
| Sample 4: Influenza B | | 22.1 | |
| Sample 5: RSV | | | 22.9 |
| Sample 6: RSV | | | 23.0 |

Example 3

Multiplexed Amplification and Detection of Influenza A and Influenza B RNA

Two-phase PCR was performed to a series of 6 samples: samples 1 and 2 had Influenza A RNA, samples 3 and 4 had Influenza B RNA, and samples 4 and 5 had both Influenza A RNA and Influenza B RNA. Each sample had outer primers at a concentration of 2 µM. No inner primers were used. Two sets of outer primers and probes were designed for the two target virus RNAs in the samples as described in Example 2. For example, a first set of outer primers and 4 probes were designed for amplifying Influenza A RNA and a second set of outer primers and 2 probes were designed for amplifying Influenza B RNA. Each sample included both of the two sets of outer primers and probes. Each of the first set of 4 probes was at a concentration of 0.4 µM and the total concentration of the 4 probes was 1.6 µM. Each of the second set of 2 probes was at a concentration of 0.3 µM and the total concentration of the 2 probes was 0.6 µM. The first set of probes designed for Influenza A RNA were attached with FAM™ dyes as the reporter and the second set of probes for Influenza B RNA were attached with Dragonfly Orange™ dyes as the reporter. Each reporter had a different fluorescence emission spectrum. The melting temperatures of the outer primers were about 75° C. to 82° C. and the melting temperatures of the probes were about 68° C. to 85° C. The total volume of each sample was 25 µL. The thermocycling profile of the two-phase PCR process for all of the samples was the following: initial steps: 50° C. for 600 seconds, 95° C. for 120 seconds; first phase: 15 cycles between 90° C. for 5 seconds and 70° C. for 5 seconds; second phase: 30 cycles between 90° C. for 5 seconds and 64° C. for 30 seconds. The amount of time for the two-phase PCR was about 32 minutes of assay time, or about 50 minutes total including the time for changing the temperatures. A typical PCR process for a traditional Influenza assay of these samples took about 110 minutes.

The detection of fluorescence signal 300 was performed for each of the two types of probes during the second phase similarly to the first example. A $C_t$ value was determined based on the detected fluorescence signal for each sample during the second phase when the fluorescence detection and/or quantification unit of thermocycler 110 was in operation, as shown in Table 3. The results show that the two-phase PCR process can perform multiplexed detection of low concentrations of viral RNAs using only outer primers within about 50 minutes, and that the two-phase PCR process according to exemplary embodiments of the present disclosure is much faster than the typical PCR process for multiplexed viral RNA detection and/or quantification.

TABLE 3

$C_t$ values of samples having Influenza A RNA, Influenza B RNA, and both Influenza A RNA and Influenza B RNA.

| Sample Tested | FAM ™ $C_t$ (Influenza A) | DFO ™ $C_t$ (Influenza B) |
| --- | --- | --- |
| Sample 1: Influenza A | 23.8 | |
| Sample 2: Influenza A | 22.4 | |
| Sample 3: Influenza B | | 18.5 |
| Sample 4: Influenza B | | 18.5 |
| Sample 5: Influenza A & B | 22.1 | 19.1 |
| Sample 6: Influenza A & B | 22.2 | 19.3 |

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments.

Moreover, while illustrative embodiments have been described herein, the scope of any and all embodiments include equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

The invention claimed is:

1. A method for amplifying nucleic acids, comprising:
preparing a reaction mixture comprising at least a first target nucleic acid and a second target nucleic acid; and
processing the reaction mixture in a thermocycler, the processing comprising:
a first phase comprising heating the reaction mixture to a first temperature and cooling the reaction mixture to a second temperature repeatedly for a first plurality of cycles; and
a second phase comprising heating the reaction mixture to a third temperature and cooling the reaction mixture to a fourth temperature repeatedly for a second plurality of cycles;
wherein the fourth temperature is gradually decreased after a predetermined number of cycles;
wherein the second temperature is higher than the fourth temperature;
wherein the reaction mixture comprises at least a first probe and a second probe; and
wherein the first probe binds to the first target nucleic acid and the second probe binds to the second target nucleic acid, both probes binding during the second phase.

2. The method of claim 1, wherein the first probe and second probe emit a first fluorescence signal and a second fluorescence signal respectively upon excitation.

3. The method of claim 2, wherein the first probe and the second probe have melting temperatures lower than the second temperature.

4. The method of claim 2, wherein the first probe has a melting temperature higher than the fourth temperature and the second probe has a melting temperature lower than the fourth temperature.

5. The method of claim 4, wherein the first fluorescence signal and the second fluorescence signal have the same emission spectrum.

6. The method of claim 5, further comprising detecting the first fluorescence signal and the second fluorescence signal during the second phase.

7. The method of claim 6, wherein the reaction mixture further comprises a first set of primers and a second set of primers that have melting temperatures around the second temperature and anneal to the first target nucleic acid and the second target nucleic acid respectively at the second temperature.

8. The method of claim 7, wherein the reaction mixture further comprises a third set of primers that anneal to the first target nucleic acid and a fourth set of primers that anneal to the second target nucleic acid, both sets of primers annealing during the second phase.

9. The method of claim 1, wherein the reaction mixture further comprises a first set of primers and a second set of primers that have melting temperatures around the second temperature and anneal to the first target nucleic acid and the second target nucleic acid respectively at the second temperature.

10. The method of claim 9, wherein the reaction mixture further comprises a third set of primers that anneal to the first target nucleic acid and a fourth set of primers that anneal to the second target nucleic acid, both sets of primers annealing during the second phase.

11. The method of claim 10, wherein the melting temperatures of the first set of primers and the second set of primers are higher than those of the third set of primers and fourth set of primers.

12. The method of claim 1, wherein both of the first temperature and the third temperature range from 85° C. to 100° C.

13. The method of claim 1, wherein the second temperature ranges from 70° C. to 85° C.

14. The method of claim 1, wherein the fourth temperature ranges from 55° C. to 70° C.

* * * * *